United States Patent [19]

Brown et al.

[11] Patent Number: 4,927,822
[45] Date of Patent: May 22, 1990

[54] 1,3,4-THIADIAZOLES

[75] Inventors: Roger C. Brown, Loughborough; John Dixon, Melton Mowbray; David H. Robinson, Shepshed, all of England

[73] Assignee: Fisons plc, Iswich, England

[21] Appl. No.: 901,048

[22] Filed: Aug. 27, 1986

[30] Foreign Application Priority Data

Aug. 31, 1985 [GB] United Kingdom ............... 8521697
Oct. 9, 1985 [GB] United Kingdom ............... 8524932
Dec. 6, 1985 [GB] United Kingdom ............... 8530143
Apr. 22, 1986 [GB] United Kingdom ............... 8609793
May 17, 1986 [GB] United Kingdom ............... 8612060

[51] Int. Cl.$^5$ .................... A61K 31/41; C07D 285/12
[52] U.S. Cl. .................... 514/236.2; 514/342; 514/363; 548/138; 548/141; 548/136; 546/277; 544/134
[58] Field of Search ............. 544/2, 9, 182, 134; 548/128, 129, 131, 132, 136, 138, 141; 514/222, 224, 227, 238, 242, 363, 364, 231.5, 236.2; 546/277

[56] References Cited

U.S. PATENT DOCUMENTS

| | | | |
|---|---|---|---|
| 4,091,024 | 5/1978 | Ondetti | 548/342 |
| 4,198,517 | 4/1980 | Ondetti | 548/344 |
| 4,254,267 | 3/1981 | Rovnyak | 548/379 |
| 4,312,990 | 1/1982 | Haugwitz | 548/379 |

FOREIGN PATENT DOCUMENTS

0048159 3/1982 European Pat. Off. ............ 548/129

OTHER PUBLICATIONS

Patchett et al, 95:25634; CA, vol. 95, 1981 p. 758.

Primary Examiner—John M. Ford
Attorney, Agent, or Firm—Marshall, O'Toole, Gerstein, Murray & Bicknell

[57] ABSTRACT

There are described compounds of formula I,

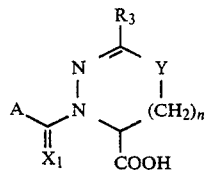

in which
Y is S, O or $NR_9$,
n is 0 or 1,
$R_9$ is hydrogen or alkyl C 1 to 10,
$R_3$ is hydrogen, alkyl C 1 to 10, cycloalkyl C3 to 10, $CF_3$, $SR_{10}$, a 5 or 6 membered heterocyclic group containing one or more S, O or N atoms, $NR_4R_5$, phenyl or phenylalkyl C7 to 12, the phenyl, phenylalkyl and heterocyclic groups optionally being fused to a further phenyl group, the heterocyclic group and any phenyl group optionally being substituted by alkyl C 1 to 6, halogen, alkoxy C 1 to 6, nitro, nitrile, $CF_3$, $SR_6$, $NR_7R_{11}$ or hydroxy,
$R_6$, $R_7$ and $R_{11}$, which may be the same or different, are each hydrogen or alkyl C 1 to 10,
$R_4$ and $R_5$, which may be the same or different, are each hydrogen, alkyl C 1 to 10 or phenyl,
$R_{10}$ is alkyl C 1 to 10,
$X_1$ is S or O, and
A is a chain comprising from 2-16 atoms, which chain carries an O or S containing substitutent at a position 2-6 atoms away from the group $C=X_1$,
and pharmaceutically acceptable salts, esters and amides thereof, p1 there are also described method of making the compounds and pharmaceutical formulations, e.g. for the treatment of hypertension, containing them.

19 Claims, No Drawings

1,3,4-THIADIAZOLES

This invention relates to new compounds, methods for their preparation and compositions containing them.

A wide variety of angiotensin converting enzyme (ACE) inhibitors are known, e.g. from French Patent Specification No. 2,372,804 and European Patent Specification No. 0012401.

We have now found a group of compounds having advantageous properties, e.g. as ACE inhibitors.

According to the invention we provide compounds of formula I.

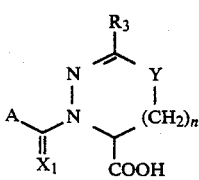

in which
Y is S, O or $NR_9$,
n is 0 or 1,
$R_9$ is hydrogen or alkyl C 1 to 10,
$R_3$ is hydrogen, alkyl C 1 to 10, cycloalkyl C3 to 10, $CF_3$, $SR_{10}$, a 5 or 6 membered heterocyclic group containing one or more S, O or N atoms, $NR_4R_5$, phenyl or phenylalkyl C7 to 12, the phenyl, phenylalkyl and heterocyclic groups optionally being fused to a further phenyl group, the heteroyclic group and any phenyl group optionally being substituted by alkyl C 1 to 6, halogen, alkoxy C 1 to 6, nitro, nitrile, $CF_3$, $SR_6$, $NR_7R_{11}$ or hydroxy,
$R_6$, $R_7$ and $R_{11}$, which may be the same or different, are each hydrogen or alkyl C 1 to 10,
$R_4$ and $R_5$, which may be the same or different, are each hydrogen, alkyl C 1 to 10 or phenyl,
$R_{10}$ is alkyl C 1 to 10,
$X_1$ is S or O, and
A is a chain comprising from 2-16 atoms, which chain carries an O or S containing substituent at a position 2-6 atoms away from the group $C=X_1$,
and pharmaceutically acceptable salts, esters and amides thereof.

According to the invention we also provide a process for the production of a compound of formula I, or a pharmaceutically acceptable salt, ester or amide thereof, which comprises (a) removal of a protecting group from a compound of formula I in which one or more of the amino or carboxylic acid groups is protected, (b) reaction of a compound of formula II,

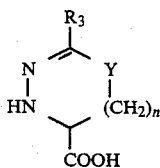

or a salt, ester, amide, tautomer, or protected derivative thereof,
in which $R_3$, Y and n are as defined above,
with a compound of formula III, $$AC(=X_1)X \qquad (III)$$

in which D and $X_1$ are as defined above, and X is a good leaving group, (c) conversion of a compound of formula I in which the asymmetric carbon atom of the Y containing heterocyclic ring is in the R configuration into a corresponding compound in which that carbon atom is in the S configuration, (d) reaction of a compound of formula II, in which $R_3$, Y and n are as defined above, with a compound of formula VI, $$AC(=X_1)OH \qquad VI$$

in which D and $X_1$ are as defined above (e) production of a pharmaceutically acceptable salt of a compound of formula I, by treating a compound of formula I, or another salt, an ester or an amide thereof, with a compound containing an available pharmaceutically acceptable ion and capable of converting the compound of formula I or the other salt, ester or amide thereof, to a pharmaceutically acceptable salt of the compound of formula I, and where desired or necessary deprotecting the resulting compound, or converting a compound of formula I to a pharmaceutically acceptable salt, ester or amide thereof or vice versa.

In process (a) the protecting group can be any convenient protecting group conventionally used in peptide synthesis and may be removed using techniques conventionally used in peptide synthesis. Thus carboxy protecting groups which may be used are alkoxy C 1 to 6, which may be a straight chain or branched alkoxy, e.g. t-butyloxy; or phenylalkoxy C7 to 12, e.g. benzyloxy. These groups can be removed by hydrolysis, for example basic hydrolysis, e.g. using aqueous methanolic sodium hydroxide; or cleavage using, for example, trifluoroacetic acid; or by hydrogenation, e.g. using palladium on charcoal. Amino-protecting groups which may be mentioned include alkyloxycarbonyl C2 to 7, e.g. t-butyloxycarbonyl or phenylalkyloxycarbonyl C8 to 13, e.g. benzyloxycarbonyl. We prefer to use starting materials in which the carboxy groups are protected.

In process (b) the group X may be halo, e.g. bromo or chloro. The reaction may be carried out in a solvent which is inert under the reaction conditions, e.g. acetonitrile, at a temperature of from 0° to 100° C., preferably at about 30° C. The reaction is preferably carried out under basic conditions, e.g. in the presence of triethylamine or polyvinylpyridine.

The reaction of process (c) may be carried out in a solvent which is inert under the reaction conditions, e.g. acetonitrile, at a temperature of from 0° C. to the boiling point of the solvent, preferably of from 20° to 30° C. The reaction may be carried out under anhydrous conditions, e.g. in the presence of molecular sieves, and in the presence of a base, e.g. pyrrolidine.

In the reaction of process (d) any conventional peptide synthesis methods may be used.

The reaction may comprise the formation of, optionally in situ, an activated derivative of an acid, e.g. an anhydride or dicyclohexylcarbodiimide derivative. The reaction may be carried out in a solvent which is inert under the reaction conditions, e.g. dichloromethane or ethyl acetate, at a temperature of from −10° C. to the boiling point of the solvent, preferably of from 0° C. to 30° C. The reaction may be carried out in the presence of a base, eg triethylamine. When the reaction involves dicyclohexylcarbodiimide it may be carried out in the presence of an activating agent, e.g. hydroxybenzotriazole.

The reaction will of course vary with the particular activated derivative used.

In process (e) the salts may be formed by reacting the free acid, or a salt, ester, amide or derivative thereof, or the free base, or a salt or derivative thereof, with one or more equivalents of the appropriate base or acid. The reaction may be carried out in a solvent or medium in which the salt is insoluble or in a solvent in which the salt is soluble, e.g. ethanol, tetrahydrofuran or diethyl ether, which may be removed in vacuo, or by freeze drying. The reaction may also be a metathetical process or it may be carried out on an ion exchange resin.

Pharmaceutically acceptable salts of the compounds of formula I include ammonium salts, alkali metal salts, e.g. sodium and potassium salts; alkaline earth metal salts, e.g. the calcium and magnesium salts; salts with organic bases, e.g. salts with dicyclohexylamine or N-methyl-D-glucamine; and salts with amino acids, e.g. with arginine, lysine etc. Also, when the molecule contains a basic group, salts with organic or inorganic acids, e.g. with HCl, HBr, $H_2SO_4$, $H_3PO_4$, methanesulfonic, toluensulfonic, maleic, fumaric or camphorsulfonic acids. The non-toxic physiologically acceptable salts are preferred, although other salts are also useful, e.g. in isolating or purifying the product.

The starting materials for the above processes are either known or may be made from known compounds using conventional processes. Thus compounds of formula II in which n is 0 may be made by reaction of a compound of formula IV,

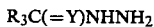
$$R_3C(=Y)NHNH_2 \qquad IV$$

or a salt thereof, in which $R_3$ and Y are as defined above, with glyoxylic acid (or a salt, ester, amide or protected derivative thereof) e.g. in an alkanol such as ethanol, at room temperature.

The compounds of formula II may exist in the tautomeric form of formula VII,

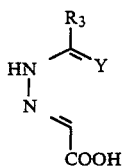

or a salt, ester, amide or protected derivative thereof, in which $R_3$ and Y are as defined above.

Compounds of formula II in which n is 1 may be made by reacting a compound of formula IV, or a salt thereof, with a compound of formula V,

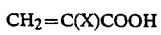
$$CH_2=C(X)COOH \qquad V$$

or a salt, ester, amide or protected derivative thereof in which X is as defined above, for example in a solvent which is inert under the reaction conditions, e.g. benzene, at a temperature of from 0° to 100° C. and preferably of from 0° to 25° C. and in the presence of a base, e.g. 1,5-diazabicyclo [4.3.0] non-5-ene.

Compounds of formula III may be made from the appropriate acid or a derivative thereof using conventional processes known per se.

The compounds of formula I, and the intermediates therefor, may be isolated from their reaction mixtures using conventional techniques known per se.

The processes described above may produce the compound of formula I or a derivative thereof. It is also within the scope of this invention to treat any derivative so produced to liberate the free compound of formula I, or to convert one derivative into another.

In addition to the processes described above the compounds of formula I may be made by a variety of processes which are analogous to those known for the production of structurally similar compounds.

We further provide the compounds of formula II and salts, esters, amides and protected derivatives thereof, which are useful as intermediates.

Pharmaceutically acceptable esters include esters with C1 to 10 alcohols, e.g. alkyl C 1 to 6 esters and esters with benzyl alcohol. The amides may be, for example, unsubstituted or mono- or di- C 1 to 6 alkyl amides and may be made by conventional techniques, e.g. reaction of an ester of the corresponding acid with ammonia or an appropriate amine.

We prefer compounds of formula I in which A is a chain comprising from 2 to 11 atoms, more preferably from 3 to 11 and most preferably from 3 to 6 atoms.

We prefer the atoms in chain A to be selected from C and N. We further prefer that less than 4 N atoms are present in the chain, more preferably less than 3 and most preferably only one. When there is one N atom in the chain we prefer it to be less than 5 atoms away from the group $C=X_1$, more preferably less than 3 atoms away and most preferably one atom away.

The chain may optionally be substituted. We prefer such substituents to be selected from alkyl C 1 to 10, phenyl and aminoalkyl C 1 to 6. We prefer the substituents to be at each or either end of the chain A. Thus when the substituent is alkyl C 1 to 10 or aminoalkyl C 1 to 6 we prefer it to be at the end adjacent the group $C=X_1$. The alkyl substituent is preferably alkyl C 1 to 6, more preferably alkyl C 1 to 3 and most preferably methyl. The aminoalkyl substituent is preferably aminoalkyl C1 to 4 and more preferably aminobutyl. When the substituent is phenyl we prefer it to be at the end of the chain A remote from the group $C=X_1$.

We prefer the O or S containing substituent to be capable of chelating organic zinc. The O or S containing substituent is preferably at a position of from 3 to 5 atoms away from the group $C=X_1$ and more preferably 3 atoms away from the group $C=X_1$. When the substituent contains 0 we prefer it to be a C=O group and more preferably a —COOH group or a derivative thereof, e.g. an alkyl C 1 to 6 ester. When the substituent contains S we prefer it to be a group —SH or a protected derivative thereof, e.g. acetylthio.

$X_1$ is preferably O.

We particularly prefer the group of compounds of formula VIII,

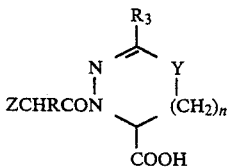

in which
- $R_3$, Y and n are as defined above,
- R is hydrogen, alkyl C1 to 10 or alkyl C1 to 6 substituted by $NH_2$,
- Z is $R_2CH(COOH)NH-$ or $R_1SCH_2-$,
- $R_1$ is hydrogen or $R_8CO-$,
- $R_2$ is alkyl C 1 to 10 or phenylalkyl C7 to 12, and
- $R_8$ is alkyl C 1 to 10 or phenyl, and pharmaceutically acceptable salts, esters and amides thereof.

We prefer those compounds of formula I in which Z is $R_2CH(COOH)NH-$.

When Z is $R_2CH(COOH)NH-$ we prefer the partial structure $-NHCHRCO-$ in formula VIII to be part of a naturally occurring amino acid. We specifically provide compounds in which Z is $R_2CH(COOH)NH-$ and the two $-COOH$ groups are in different forms, e.g. where one is esterified and the other is not. We also prefer the group COOH in the substituent Z to be in the form of an ester or amide, e.g. to be an alkyl C 1 to 6 ester, preferably an ethyl ester. We further prefer the carbon atom to which the group COOH or its derivative in the substituent Z is attached to be in the S configuration.

Where any of R, $R_2$, $R_3$, $R_4$, $R_5$, $R_6$, $R_7$, $R_8$, $R_9$, $R_{10}$ or $R_{11}$ represent alkyl they may individually be straight, branched or cycloalkyl, e.g. containing up to and including 6 carbon atoms. We prefer R to be alkyl C 1 to 6 or aminoalkyl C 1 to 6. When R is unsubstituted alkyl C 1 to 6 we prefer R to be methyl. When R is aminoalkyl C 1 to 6 we prefer the $NH_2$ group to be at the end of an unbranched chain, in particular we prefer R to be the group $-CH_2CH_2CH_2CH_2NH_2$. We further prefer the carbon atom to which R is attached to be in the S configuration.

When $R_2$ is alkyl we prefer it to be a straight chain alkyl, preferably a C 1 to 6 alkyl, most preferably n-propyl. When $R_2$ is phenylalkyl C7 to 12 we prefer the alkyl chain to comprise 1 to 3 carbon atoms. In particular, when $R_2$ is phenylalkyl, we prefer $R_2$ to be phenylethyl.

We prefer $R_8$ to be alkyl C 1 to 10, more preferably alkyl C1 to 6 and most preferably methyl.

We prefer $R_{10}$ to be alkyl C 1 to 6 and more preferably methyl.

Where $R_3$ represents alkyl it may be straight, branched or cycloalkyl, e.g. containing up to and including 10 carbon atoms. The term cycloalkyl includes any mono-, bi- or tri-cyclic alkane. When $R_3$ represents a 5 membered heterocyclic group we prefer only one heteroatom to be present. When $R_3$ represents a 6 membered heterocyclic group we prefer one or two heteroatoms to be present, preferably selected from N and O. Examples of $R_3$ are methyl, pyridyl, furyl, methoxy, methylthio, t-butyl, isopropyl, cyclohexyl, morpholinyl, adamantyl, methylamino, benzyl, naphthyl and phenyl optionally substituted by methylthio, methoxy, methyl, ethyl, chloro or $CF_3$.

We prefer $R_3$ to be alkyl C 1 to 10 or cycloalkyl C3 to 10, more preferably alkyl C 1 to 6 or cycloalkyl C3 to 6. We particularly prefer $R_3$ to be either t-butyl or cyclohexyl.

Y is preferably O, or more preferably S.

We prefer n to be 0.

We prefer the $-COOH$ substituent on the Y containing heterocyclic ring to be underivatised. We further prefer the asymmetric carbon atom of the Y containing heterocyclic ring to be in the S configuration.

$R_1$ is preferably hydrogen.

We particularly prefer the specific group of compounds of formula VIII in which Z is $R_2CH(COOH)NH-$, Y is S, R is methyl or aminobutyl, n is O, $R_2$ is n-propyl or phenylethyl and $R_3$ is t-butyl and pharmaceutically acceptable salts, esters and amides thereof.

The preferred salts of the compounds of formula VIII are maleates, hydrochlorides, ammonium salts or dicyclohexyl- ammonium salts.

The compounds of formula I may contain one or more asymmetric carbon atoms and may therefore exhibit optical and/or diastereo isomerism. Diastereoisomers may be separated using conventional techniques, e.g. chromatography or fractional crystallisation. The various optical isomers may be isolated by separation of a racemic or other mixture of the compounds using conventional, e.g.. fractional crystallisation or HPLC, techniques. Alternatively the desired optical isomers may be made by reaction of the appropriate optically active starting materials under conditions which will not cause racemisation. We prefer those compounds of formula I and formula VIII in which any asymmetric carbon atoms are in the S configuration.

The compounds of the invention are advantageous in that they are more efficaceous, produce less side effects, are longer acting, more readily absorbed, less toxic, distributed in the body tissues in a different manner or have other advantageous properties when compared to compounds of similar structure.

The compounds of the invention are useful because they possess pharmacological properties. In particular they inhibit angiotensin converting enzyme and thus block conversion of the decapeptide angiotensin I to angiotensin II (see Example A). Angiotensin II is a potent vasoconstrictor in mammals. It also stimulates aldosterone release which results in salt and fluid retention. Increased blood pressure is the physiological result of these changes. Inhibitors of angiotensin converting enzyme are thus effective antihypertensive agents in a variety of animal models (see Example B) and are indicated for use clinically, for example, in patients with renovascular, malignant or essential hypertension or chronic congestive heart failure. See, for example, D W Cushman et al., *Biochemistry* 16, 5484 (1977) and E W Petrillo and M A Ondetti, Med. Res. Rev. 2 93 (1982).

Thus, the compounds of this invention are useful as antihypertensives in treating hypertensive mammals, including humans and they can be utilised to achieve reduction of blood pressure, e.g. in formulations containing appropriate pharmaceutically acceptable excipients, diluents or carriers. The compounds of the invention can be administered (to animals or humans) in unit dosages of 1 to 500mg generally given several times, eg 1 to 4 times, per day thus giving a total daily dose of from 1 to 2000 mg per day. The dose will vary depending on the type and severity of disease, weight of patient and other factors which a person skilled in the art will recognize.

The compounds of this invention may be given in combination with other pharmaceutically active compounds, eg diuretics or antihypertensives. The dosage of the other pharmaceutically active compound can be that conventionally used when the compound is administered on its own, but is preferably somewhat lower. To illustrate these combinations, one of the antihypertensives of this invention effective clinically in the range, e.g. 1–200 milligrams per day, can be combined at levels ranging, e.g. from 1–200 milligrams per day with the following antihypertensives and diuretics in dose ranges per day as indicated:

hydrochlorothiazide (15–200mg), chlorothiazide (125–2000mg), ethacrynic acid (15–200mg), amiloride (5–20mg), furosemide (5–80mg), propanolol (20–480mg), timolol (5–50mg) nifedipine (20–100mg), verapamil (120–480mg) and methyldopa (65–2000mg). In addition, the triple drug combinations of hydrochlorothiazide (15–200mg) plus amiloride (5–20mg) plus converting enzyme inhibitor. of this invention (1–200mg) or hydrochlorothiazide (15–200mg) plus timolol (5–50mg), plus the converting enzyme inhibitor of this invention (1–200mg) are contemplated. The above dose ranges may be adjusted on a unit basis as necessary to permit divided daily dosage. Also, the dose may vary depending on the severity of the disease, weight of patient and other factors which a person skilled in the art will recognize.

According to our invention we also provide a pharmaceutical composition comprising preferably less than 80%, more preferably less than 50%, e.g. 1 to 20%, by weight of a compound of formula I, or a pharmaceutically acceptable salt or ester thereof, in admixture with a pharmaceutically acceptable adjuvant, diluent or carrier.

Thus the compound may be put up as a tablet, capsule, dragee, suppository, suspension, solution, injection, implant, a topical, e.g. transdermal, preparation such as a gel, cream, ointment, aerosol or a polymer system, or an inhalation form, e.g. an aerosol or a powder formulation.

We prefer compositions which are designed to be taken oesophageally and to release their contents in the gastrointestinal tract. Thus we prefer tablets which may, for example, be made by direct compression. In such a process the active ingredient is mixed with one or more of modified forms of starch, calcium phosphate, a sugar e.g. lactose, microcrystalline cellulose and/or other directly compressible excipients, together with lubricant(s), e.g. stearic acid or magnesium stearate, flow aid(s), e.g. talc or colloidal silicon dioxide, and disintegrant(s), e.g. starch or the materials sold under the Trade Marks, Nymcel, Ac-Di-Sol, Explotab and Plasdone XL. Tablets are then formed by direct compression, and may be sugar or film coated e.g. with hydroxypropylmethylcellulose.

Alternatively the active ingredient may be granulated before tabletting. In such cases the active ingredient is mixed with one or more of starch, calcium phosphate, a sugar e.g. lactose, microcrystalline cellulose or other suitable excipients and granulated with a binder such as starch, pregelled starch, polyvinylpyrrolidone, gelatine, a modified gelatine, or a cellulose derivative, e.g. hydroxypropylmethylcellulose. The mass is then dried, sieved and mixed with lubricant(s), flow aid(s) and disintegrant(s), such as described in the previous paragraph. Tablets are then formed by compression of the granules, and may be sugar or film coated, e.g. with hydroxypropylmethylcellulose.

As a further alternative a powder, blend or granules, such as are described above as intermediates in tabletting, may be filled into a suitable, e.g. gelatine, capsule.

In order to improve the bioavailability, or decrease variability of availability, of the active ingredient the compound may be:

(a) dissolved in a suitable solvent, e.g. polyethylene glycol, Gelucaire, arachis oil, a (hydrogenated) vegetable oil or beeswax and the solution is then filled into a gelatine capsule.

(b) produced as a spray-dried or freeze-dried form prior to mixing with other excipients, (c) milled and/or micronised to produce a powder with a large surface area prior to mixing with other excipients, (d) made into a solution and distributed over an inert excipient having a large surface area, e.g. colloidal silicon dioxide. The solvent is evaporated and further excipients added, (e) formed into a complex with cyclodextrin prior to mixing with other excipients. This complex also assists in increasing light stability, or (f) made into a solid solution or co-precipitated, e.g. with polyvinylpyrrolidone, polyethyleneglycol, modified cellulose, hydroxypropylmethylcellulose, urea or a sugar prior to mixing with further excipients.

The compounds, either in their normal form or in a modified form, e.g. as described immediately above, may be formulated in a controlled release form. Thus the compound may be dispersed, or contained in, a polymer matrix formed from, for example, ethylcellulose, hydroxypropylmethylcellulose or the product sold under the Trade Mark Eudragit. Alternatively the compound may be formulated as a tablet or beads which are surrounded by a semi-permeable membrane, e.g. shellac, ethylcellulose or an acrylate/methacrylate polymer.

Certain of the compounds of formula I can form hydrates or solvates, e.g. with an alcohol such as ethanol or, for example when Y is NH can exist in tautomeric forms.

The invention is illustrated, but in no way limited by the following Examples in which temperatures are in degrees centigrade.

EXAMPLE 1

3-[N-(1-(S)-Ethoxycarbonyl-3-phenylpropyl)-L-alanyl]-2,3-dihydro-5-phenyl-1,3,4-thiadiazole-2-(S)-carboxylic acid (a) Benzyl 2,3-dihydro-5-phenyl-1,3,4-thiadiazole-2-carboxylate A solution of benzenecarbothioic acid hydrazide (2g) and benzyl glyoxylate (2.6g) in ethanol (5ml) was stirred at room temperature for 18 hours under nitrogen. The solvent was removed by evaporation and the residue was flash chromatographed to yield the sub-title product (3.5g) as a beige solid.

A mass spectrum showed M+ 298 (base peak 16).
$C_{16}H_{14}N_2O_2S$ requires MWt 298.

(b) Benzyl 3-[N-(1-(S)-ethoxycarbonyl-3phenylpropyl)-L-alanyl]-2,3-dihydro-5-phenyl-1,3,4-thiadiazole-2-(R)-carboxylate A stirred mixture of N-(1-(S)-ethoxycarbonyl-3-phenylpropyl)-L-alanine (3.1 g) and 1-hydroxybenzotriazole (1.7g) in dichloromethane (100ml) was treated with a solution of the product of step (a) (6.85g) in dichloromethane (25ml). A solution of dicyclohexylcarbodiimide (2.26g) in dichloromethane (20ml) was added over 20 minutes and the mixture was stirred at room temperature for 2 days under nitrogen.

The suspended solid was filtered, the filtrate evaporated and the residue was purified by flash chromatography to give the sub-title product (5.23g) as a gum.

A fast atom bombardment mass spectrum showed $M^+560$ (base peak 91).

$C_{31}H_{33}N_3O_5S$ requires MWt 559.

(c) Benzyl 3-[N-(1-(S)-ethoxycarbonyl-3-phenylpropyl)-L-alanyl]-2,3-dihydro-5-phenyl-1,3,4-thiadiazole-2-(S)-carboxylate A solution of the product from step (b) (0.16g), pyrrolidine (0.16ml) and 3A molecular sieves (0.2g) in acetonitrile (3.2ml) was stirred at room temperature for 3.5 hours. The mixture was poured into water and extracted with ether, dried over magnesium sulphate and evaporated. The residue was flash chromatographed to give the sub-title product (0.05g) as a gum.

A fast atom bombardment mass spectrum showed $M^+560$ (base peak 91).

$C_{31}H_{33}N_3O_5S$ requires MWt 559.

(d) 3-[N-(1-(S)-Ethoxycarbonyl-3-phenylpropyl)-L-alanyl]-2,3-dihydro-5-phenyl-1,3,4-thiadiazole-2-(S)-carboxylic acid A solution of the product from step (c) (0.26g) in ethanol (20ml) was treated with 10% palladium on charcoal (0.1g) and stirred in a pressure vessel under hydrogen at 3 atmospheres at room temperature for 3 days. The catalyst was filtered off and the filtrate evaporated. The residue was triturated with ether to give the title product (0.08g) as a white solid, m.p. 180.5°–182°.

A mass spectrum (FAB) showed $M^+470$ (base peak 234).

$C_{24}H_{27}N_3O_5S$ requires MWt 469.

EXAMPLE 2

3-[N-(1-(S)-Ethoxycarbonyl-3-phenylpropyl)-L-alanyl]-2,3-dihydro-5-phenyl-1,3,4-thiadiazole-2-(R)-carboxylic acid A solution of the product from Example 1, step (b) (0.43g) in ethanol (100ml) was treated with 10% palladium on charcoal (0.1g) and stirred in a pressure vessel under hydrogen at 3 atmospheres at room temperature for 3 days. The catalyst was filtered off and the filtrate evaporated. The residue was triturated with a mixture of ether and petroleum ether (bp 40°–60°) to give the title product (0.19g) as a pale grey, non-crystalline solid.

A mass spectrum (FAB) showed $M^+470$ (base peak 234).

$C_{24}H_{27}N_3O_5S$ requires MWt 469.

EXAMPLE 3

2,3-Dihydro-3-(3-mercapto-1-oxopropyl)-5-phenyl-1,3,4-thiadiazole-2-carboxylic acid (a) Ethyl 2,3-dihydro-5-phenyl-1,3,4-thiadiazole-2-carboxylate A solution of benzenecarbothioic acid hydrazide (0.4g) and ethyl glyoxylate (0.4g) in ethanol (1 ml) was stirred at room temperature for 2 hours. The solvent was removed by evaporation and the residue re-evaporated with toluene (x2) to yield the sub-title product (0.7g) as a gum.

A mass spectrum showed $M^+236$ (base peak 163).

$C_{11}H_{12}N_2O_2S$ requires MWt 236.

(b) Ethyl 3-(3-acetylthio-1-oxopropyl)-2,3-dihydro-5-phenyl-1,3,4-thiadiazole-2-carboxylate A solution of the product of step (a) (2.36g) in toluene (100ml) was treated with polyvinylpyridine (2.0g) and 3-acetylthiopropanoyl chloride (1.7g) and the mixture stirred at room temperature for 4 hours. The mixture was filtered and the filtrate stirred with a saturated solution of sodium bicarbonate (100ml) for 1 hour. The organic phase was separated, washed with water, dried and evaporated to a gum. The residue was purified by flash chromatography to give the sub-title product (2.62g) as an oil.

A mass spectrum showed $M^+366$ (base peak 163).

$C_{16}H_{18}N_2O_4S_2$ requires MWt 366.

(c) 2,3-Dihydro-3-(3-mercapto-1-oxopropyl)-5-phenyl-1,3,4-thiadiazole-2-carboxylic acid A solution of the product of step (b) (2.6g) in methanol (20ml) was cooled to 0° under nitrogen and treated dropwise with a solution of potassium hydroxide (1.42g) in water (8ml). The mixture was allowed to warm to room temperature over 2 hours and then partitioned between ethyl acetate and water. The aqueous phase was acidified with 2N HCl and the organic phase separated, washed with water and dried. Evaporation yielded an oil which slowly crystallised to give the title product (0.7g) as white crystals. mp 145°–6°.

Found: C 48.54, H 4.17, N 9.49, S21.68%. $C_{12}H_{12}N_2O_3S_2$ requires: C 48.65, H 4.05, N 9.46, S21.62%.

EXAMPLE 4

5-t-Butyl-3-[N-(1-(S)-ethoxycarbonyl-3-phenylpropyl)-L-alanyl]-2,3-dihydro-1,3,4-thiadiazole-2-(S)-carboxylic acid (a) Benzyl 5-t-butyl-2,3-dihydro-1,3,4-thiadiazole-2-carboxylate A solution of t-butylcarbothioic acid hydrazide (0.7g) and benzyl glyoxylate (1g) in ethanol (15ml) was stirred under nitrogen for 16 hours. The solvent was removed by evaporation and the residue was purified by flash chromatography (petroleum ether/ethyl acetate eluent) to yield the sub-title product (1.1g) as a gum.

(b) Benzyl 5-t-butyl-3-[N-(1-(S)-ethoxycarbonyl-3-phenylpropyl)-L-alanyl]-2,3-dihydro-1,3,4-thiadiazole-2-(R)-carboxylate A stirred mixture of N-(1-(S)-ethoxycarbonyl-3-phenylpropyl)-L-alanine (0.57g) and 1-hydroxybenzotriazole (0.28g) in dichloromethane (40ml) was treated with a solution of the product of step (a) (1.14g) in dichloromethane (5ml). Dicyclohexylcarbodiimide (0.42g) was added and the mixture stirred at room temperature for 16 hours under nitrogen. The suspended solid was removed by filtration and the filtrate evaporated to a gum. The residue was purified by flash chromatography to give the sub-title product (0.82g) as an oil.

A mass spectrum (FAB) showed $M^+540$ (base peak 91).

$C_{29}H_{37}N_3O_5S$ requires MWt 539.

(c) Benzyl 5-t-butyl-3-[N-(1-(S)-ethoxycarbonyl-3-phenyl ropyl)-L-alanyl]-2,3-dihydro-1,3,4-thiadiazole-2-(S)-carboxylate A solution of the product from step (b) (1.0g) and pyrrolidine (1g) in dry acetonitrile (30ml) was treated with crushed 3A molecular seives and the mixture stirred at room temperature for 6 hours. The volatile materials were removed by evaporation and the S,S,S isomer separated from the more polar S,S,R isomer by flash chromatography (petroleum ether/ethyl acetate eluent). The sub-title product (0.4g) was isolated as a clear gum.

A mass spectrum showed M+539 (base peak 234).
$C_{29}H_{37}N_3O_5S$ requires MWt 539.

(d) 5-t-Butyl-3-[N-(1-(S)-ethoxycarbonyl-3-phenylpropyl)-L -alanyl]-2,3-dihydro-1,3,4-thiadiazole-2-(S)-carboxylic acid A solution of the product from step (c) (0.67g) in ethanol (100ml) was treated with 10% palladium on carbon (0.6g) and the mixture stirred under 1 atmosphere of hydrogen for 16 hours. The catalyst was removed by filtration and the filtrate reduced in volume to ca. 2ml by evaporation. The cooled solution yielded the title product (0.3g) as white crystals, mp 165°-8°.

Found C,58.87; H,6.89; N,9.34; S,21%. $C_{22}H_{31}N_3O_5S$ requires: C,58.80; H,6.90; N,9.35; S,7.13%.

A mass spectrum (FAB) showed M+450 (base peak 234).
$C_{22}H_{31}N_3O_5S$ requires MWt 449.

EXAMPLE 5

5-t-Butyl-3-[N$_2$-(1-(S)-carboxy-3-phenylpropyl)-L -lysyl]-2,3-dihydro-1,3,4-thiadiazole-2-(S)-carboxylic acid (a) Benzyl 2-hydroxy-4-phenylbutanoate A solution of 2-hydroxy-4-phenylbutanoic acid (20.4g), triethylamine (15.9ml) and benzyl bromide (12.75ml) in ethyl acetate (64ml) was heated under reflux for 16 hours. The solution was cooled and poured into a mixture of water and ether. The separated organic extract was washed with saturated sodium bicarbonate solution and water, dried over magnesium sulphate and filtered. The filtrate was evaporated and the residue purified by flash chromatography (petroleum ether/ethyl acetate eluent) to yield the sub-title product as a yellow oil (14g).

A mass spectrum showed M+270 (base peak 91).
$C_{17}H_{18}O_3$ requires MWt 270.

(b) N$^6$-Benzyloxycarbonyl-N$^2$-(1-(S)-benzyloxycarbonyl-3-phenylpropyl)-L-lysine hydrochloride A solution of the product from step (a) (13.8g) and pyridine (6.6ml) in dichloromethane (136ml) was added over 0.5 hours under nitrogen to a stirred solution of trifluoromethanesulphonic anhydride (12.9ml) in dichloromethane (136ml) cooled to 5° C. After a further 0.5 hours the solution was washed with water, dried over magnesium sulphate, filtered and the filtrate evaporated.

The residue was taken up in dichloromethane (136ml) and added to a solution of N$^6$-benzyloxycarbonyl-L-lysine t-butyl ester (15.5g) and triethylamine (6.5ml) in dichloromethane (136ml). The mixture was stirred at room temperature for 1 hour, heated under reflux for 2.5 hours, cooled, washed with water, dried over magnesium sulphate and filtered. The filtrate was evaporated and the residue purified by flash chromatography (ether/petroleum ether eluent) to separate and isolate the more polar SS isomer.

A solution of the SS t-butyl ester (0.5g) in ether (15ml) was cooled to +5° and saturated with hydrogen chloride for 2 hours. The solution was stirred at room temperature for a further 18 hours and the solvent was then removed by evaporation. Trituration of the residue in ether gave the sub-title product as a white solid (0.39g).

A fast atom bombardment mass spectrum showed M+533 (base peak 91).
$C_{31}H_{36}N_2O_6$ requires MWt 532.

(c) Benzyl 3-[N$_6$-benzyloxycarbonyl-N$_2$-(1-(S) -benzyloxycarbonyl-3-phenylpropyl)-L-lysyl]-5-t-butyl-2,3 -dihydro-1,3,4-thiadiazole-2-(R)-carboxylate A stirred solution of the SS product from step (b) (5.68g) and 1-hydroxybenzotriazole (1.35g) in dichloromethane (85ml) was treated with a solution of the product of Example 4, step (a) (5.87g) in dichloromethane (60ml). A solution of dicylohexylcarbodiimide (2.1g) in dichloromethane (85ml) was added over 5 minutes and the mixture was stirred at room temperature for 18 hours under nitrogen. Triethylamine (1.4ml) was added and the suspended solid removed by filtration. The filtrate was evaporated and the residue purified by flash chromatography to give the sub-title product as an oil (2.1g).

A fast atom bombardment mass spectrum showed M+793 (base peak 91).
$C_{45}H_{52}N_4O_7S$ requires MWt 792.

(d) Benzyl 3-[N$_6$-benzyloxycarbonyl-N$_2$-(1-(S) -benzyloxycarbonyl-3-phenylpropyl)-L-lysyl]-5-t-butyl-2,3-dihydro-1,3,4-thiadiazole-2-(S)-carboxylate A solution of the product of step (c) (2.1g) and pyrrolidine (1.6ml) in dry acetonitrile (60ml) was treated with crushed 3A molecular sieves and the mixture stirred at room temperature for 24 hours under nitrogen. The volatile materials were removed by evaporation and the SSS isomer separated from the more polar SSR isomer by flash chromatography. The SSS sub-title product (0.47g) was isolated as a clear oil.

A fast atom bombardment mass spectrum showed M+793 (base peak 91).
$C_{45}H_{52}N_4O_7S$ requires MWt 792.

(e) 5-t-Butyl-3-[N$_2$-(1-(S)-carboxy-3-phenylpropyl)-L -lysyl]-2,3-dihydro-1,3,4-thiadiazole-2-(S)-carboxylic acid A solution of the product from step d) (1.1g) in ethanol (90ml) was treated with 10% palladium on carbon (0.9g) and the mixture stirred under 1 atmosphere of hydrogen for 1 hour. The catalyst was removed by filtration and the filtrate evaporated. The residue was recrystallised from a mixture of tetrahydrofuran and ethanol to give the title product as a white solid (0.24g) mp slowly decomposes at 180°-190°.

Found: C 55.86 H 6.97 N 11.24 S 6.56 H$_2$O 2.83 $C_{23}H_{34}N_4O_5S$. 0.77H$_2$O.
Requires: C 56.11 H 7.23 N 11.39 S 6.51 H$_2$O 2.82.

A fast atom bombardment mass spectrum showed M+479 (base peak 84).
$C_{23}H_{34}N_4O_5S$ requires MWt 478.

EXAMPLE 6

5-t-Butyl-3-[N-(1-(S)-ethoxycarbonylbutyl)-L-alanyl]- 2,3-dihydro-1,3,4-thiadiazole-2-(S)-carboxylic acid (a) Ethyl 2-([(trifluoromethyl)sulphonyl]oxy)pentanoate Under nitrogen, a solution of pyridine (11.9g) in dry dichloromethane (500ml) was rapidly stirred at −22° while trifluoromethane sulphonic anhydride (40.5g) was added dropwise. After the addition, the white slurry was stirred at −22° for 15 minutes and then a solution of ethyl 2-hydroxy pentanoate (16.8g) in dichloromethane was added over 2 minutes at this temperature. The temperature was then allowed to rise to room temperature and the mixture was stirred vigorously for 1 hour, after which time the white solid was filtered off, washed well with dichloromethane and the combined washings and filtrate were evaporated to dryness. The oily solid obtained was taken up in 60°–80° petroleum ether and was passed down a short pad of silica, eluting with more petroleum ether. The petroleum ether solution was evaporated to dryness leaving an oil (23.4g)

NMR, CDCl$_3$,delta: 1.0(3H,t,) 1.32(3H,t,) 1.5(2H,m), 2.0(2H,m), 4.3(2H,m) 5.12(1H,t).

(b) N-(1-Ethoxycarbonylbutyl)-L-alanine benzyl ester

L-Alanine benzyl ester hydrochloride (10.0g) was converted to the free-base in dichloromethane using triethylamine. The resulting mixture was evaporated to dryness and the residue was slurried with several portions of diethyl ether. The combined ether solutions were evaporated to dryness leaving the free-base as an oil.

The oil was dissolved in dichloromethane (200ml) and triethylamine (7.2g) was added. The resulting solution was stirred under nitrogen at room temperature while a solution of the product from step (a) (12.8g) in dichloromethane was added dropwise over 30 minutes. The resulting mixture was stirred for 2 hours at room temperature, for 2 hours at reflux and then was evaporated to dryness leaving an oily residue which was purified by flash chromatography on silica eluting with 60°–80° petroleum ether/diethyl ether 5:1 to give the R,S, (4.8g, 34%) and S,S, (4.7g, 33%) diastereoisomer in order of elution

| | |
|---|---|
| R,S | |
| NMR CDCl$_3$,delta, | 0.9 (3H,t), 1.24 (3H,t), 1.30 (3H,d) 1.38 (2H,m), 1.6 (2H,m), 3.27 (1H,t) 3.4 (1H,q), 4.12 (2H,m), 5.15 (2H,q), 7.35 (5H,s). |
| S,S | |
| NMR CDCl$_3$,delta: | 0.9 (3H,t); 1.28 (3H,t); 1.38 (3H,d); 1.3–1.8 (4H,m); 3.28 (1H,t); 3.4 (1H,q); 4.18 (2H,m); 5.17 (2H,q); 7.35 (5H,s). |

(c) N-(1-(S)-Ethoxycarbonylbutyl)-L-alanine

The S,S diastereoisomer benzylester from step (b) (6.2g) in ethanol (250ml) was hydrogenated at 3 atmospheres at room temperature for 30 minutes over 10% palladium on charcoal (0.6g). The catalyst was removed by filtration and the filtrate was evaporated to near dryness. The residue was slurried with diethyl ether and the white solid was filtered off and was dried to give the required product (3.8g) mp 153°–4°.

Found: C,55.62; H, 8.47: N, 6.32%. C$_{10}$H$_{19}$NO$_4$ requires: C,55.29; H,8.75; N,6.45%.

(d) Benzyl 5-t-butyl-3-[N-(1-(S)-ethoxycarbonylbutyl)-L -alanyl]-2,3-dihydro-1,3,4-thiadiazole-2-(R)-carboxylate Under nitrogen at room temperature a mixture of the S,S amino acid from step c) (0.62g) and 1-hydroxybenzotriazole (0.45g) in dry dichloromethane (125ml) was stirred for 30 minutes with benzyl 5-t-butyl-2,3-dihdro-1,3,4-thiadiazole-2-carboxylate (1.6g). Dicyclohexylcarbodiimide (0.6g) was then added and the resulting mixture was stirred for 18 hours, filtered and the filtrate evaporated to dryness. The residue was purified by column chromatography on silica eluting with diethyl ether/petroleum ether (60°–80°), 1:1 to give the required diester as an oil (1.1g)

NMR CDCl$_3$,delta: 0.9(3H,t), 1.2–1.7(19H,m), 3.3(1H,t) 4.2(3H,m), 5.2(2H,q), 6.18(1H,s) 7.35(5H,s).

(e) Benzyl 5-t-butyl-3-[N-(1-(S)-ethoxycarbonylbutyl)-L -alanyl]-2,3-dihydro-1,3,4-thiadiazole-2-(S)-carboxylate Under nitrogen, pyrrolidine (1.5ml) was added to a solution of the 'S,S,R' ester (step d) (1.6g) and the resulting solution was stirred at room temperature for 24 hours. The 1:1 mixture of S,S,R and S,S,S esters so produced was separated by flash chromatography on silica eluting with ethyl acetate/petroleum ether 60°–80°, 1:3 to give 0.65g of each isomer. The S,S,R isomer was recycled such that the total conversion was 81%.

NMR CDCl$_3$,delta: 0.9(3H,t), 1.2–1.7(19H,m), 3.3(1H,t) 4.2(3H,m), 5.17(2H,s), 6.18(1H,s) 7.35(5H,s).

(f) 5-t-Butyl-3-[N-(1-(S)-ethoxycarbonylbutyl)-L-alanyl]-2, 3-dihydro-1,3,4-thiadiazole-2-(S)-carboxylic acid The S,S,S benzyl ester from step (e) (1.8g) in ethanol (500ml) was hydrogenated over 10% Pd on charcoal (1.8g) at atmospheric pressure and room temperature for 5 hours. The catalyst was removed by filtration and the filtrate was evaporated to dryness. The residue was triturated with a 1:1 mixture of ether/petroleum ether 60°–80° to give the required acid as a white solid (1.3g). mp 183°–5°.

Found: C, 47.13; H, 7.89; N, 9.31; S, 7.12%. C$_{17}$H$_{29}$N$_3$O$_5$S. 2.5 H$_2$0 requires: C, 47.22; H, 7.87; N,9.72; S, 7.41%.

EXAMPLE 7

3-[N-(1-(S)-Ethoxycarbonyl-3-phenylpropyl)-L-alanyl]-2,3-dihydro-5-[4-(methylthio)phenyl]-1,3,4-thiadiazole-2-(S)-carboxylic acid (a) 1-[(4-(Methylthio)phenyl)thioxomethyl]pyrrolidine A mixture of 4-(methylthio)benzaldehyde (50.0g) and sulphur (15.8g) was cooled to 0° and pyrrolidine (41.1ml) was added over 30 minutes. On complete addition the whole was heated under reflux for 1.5 hours. The mixture was poured, whilst warm, into ethanol (250ml) and the resulting solid filtered off. Recrystallization from ethanol afforded the sub-title compound as a fawn, crystalline solid, (71.3g). mp 116.5°–118°.

(b) 4-[4-(Methylthio)phenyl]-4-(pyrrolidinium-1-ylidene)-3-thiobutanoic acid bromide A solution of the product of step (a) (20.0g) and bromoacetic acid (12.9g) in benzene (100ml) was stirred at room temperature under nitrogen for 18 hours. The resulting precipitate was filtered off and washed with ether to yield the sub-title compound (28.6g) as a white solid. mp 157°–158°.

(c) [((4-(Methylthio)phenyl)thioxomethyl)thio]acetic acid

Hydrogen sulphide was passed through a solution of the product of step (b) (25.0g) in methanol (250ml) and cooled in an ice bath, for a period of 3 hours.

After standing at 0° for 18 hours the solvent was removed under reduced pressure and the residue was triturated with water. The solid was filtered off and recrystallised from petroleum ether to afford the sub-title compound (16.7 g) as a red crystalline solid. mp 117°.

(d) 4-(Methylthio)phenylcarbothioic acid hydrazide

To a solution of the product of step c) (15.0 g) in methanol (200 ml) was added aqueous potassium hydroxide (58.0 ml, 1M) followed by hydrazine monohydrate (3.1 ml) dropwise over 30 minutes. After stirring at room temperature for 1 hour the mixture was acidified to pH 5 with concentrated hydrochloric acid. The resulting precipitate was filtered off and recrystallised from ethanol to afford the sub-title compound (9.9 g) as pale yellow plates. mp 152°–153°.

(e) t-Butyl 2,3-dihydro-5-[4-(methylthio)phenyl]-1,3,4-thiadiazole-2-carboxylate The product of step d) (3.0 g) was stirred at room temperature under nitrogen with t-butyl glyoxylate (2.0 g) in methanol (100 ml) for 18 hours. The mixture was evaporated and the residue purified by flash chromatography (ether/petroleum ether 1:3) to afford the sub-title compound (3.9 g) as a pale yellow solid. mp 71°–72°.

(f) t-Butyl 3-[N-(1-(S)-ethoxycarbonyl-3-phenylpropyl)-L-alanyl]-2,3-dihydro-5-[4-(methylthio)phenyl]-1,3,4-thiadiazole-2-(S)-carboxylate Prepared from the product of step e) and N-(1-(S)-ethoxycarbonyl-3-phenylpropyl)-L-alanine by similar processes to those of Example 1, steps b and c as a yellow oil.

A mass spectrum (FAB) showed M+572 (base peak 234) $C_{29}H_{37}N_3S_2$ requires 571.

(g) 3-[N-(1-(S)-Ethoxycarbonyl-3-phenylpropyl)-L-alanyl]-2,3-dihydro-5-[4-(methylthio)phenyl]-1,3,4-thiadiazole-2-(S)-carboxylic acid A solution of the product (1.0 g) from step (f) in dry diethyl ether (50 ml) was saturated with hydrogen chloride for 3 hours. The solvent was evaporated and the residue was purified by chromatography to give the title compound (0.1 g) as a pale yellow solid. mp 163°–164°

Found: C, 57.46; H, 5.53; N, 8.01; S, 12.14. $C_{25}H_{28}N_3O_5S_2$. 0.5 $H_2O$ requires: C, 57.25; H, 5.72; N, 8.01; S, 12.21.

EXAMPLE 8

Ammonium 2,3-dihydro-3-(3-mercapto-2-(S)-methyl-1-oxopropyl)-5-phenyl-1,3,4-thiadazole-2-(S)-carboxylate monohydrate (a) Benzyl 3-(3-acetylthio-2-(S)-methyl-1-oxopropyl)-2,3-dihydro-5-phenyl-1,3,4-thiadiazole-2-carboxylate 3-Acetylthio-2-(S)-methylpropanoyl chloride (2.3 g) in dichloromethane (30 ml) was added over 5 minutes to a stirred mixture of the product of Example 1, step a) (3.6 g) and polyvinylpyridine (2.4 g) in dichloromethane (60 ml). The mixture was stirred at room temperature for 20 hours and 3-acetylthio-2-(S)-methylpropanoyl chloride (1.2 g) was then added. The mixture was stirred for a further 2 hours, filtered and the filtrate stirred with a saturated solution of sodium bicarbonate for 1 hour. The organic phase was separated, washed with water, dried and evaporated to a gum. The residue was purified by flash chromatography to give the sub-title product (4.4 g) as an oil.

(b) Ammonium 2,3-dihydro-3-[3-mercapto-2-(S)-methyl-1-oxopropyl]-5-phenyl-1,3,4-thiadiazole-2-(S)-carboxylate A solution of the product of step a) (2.8 g) in methanol (50 ml) under nitrogen was treated dropwise with a solution of potassium hydroxide (1.3 g) in water (100 ml). The mixture was stirred for a further 4 hours and then partitioned between ether and water. The separated aqueous phase was acidified with 2N HCl and extracted with ether. The organic phase was washed with water, dried and evaporated to an oil. The residue was purified by reverse phase HPLC to give the title product (0.023 g) as a white solid. mp 194°–7°.

A mass spectrum showed $M^{30}310$ (base peak 163). $C_{13}H_{14}N_2O_3S_2$ Requires MWt 310.

EXAMPLE 9

2-Cyclohexyl-5,6-dihydro-4-(3-mercapto-1-oxopropyl)-4H-1,3,4-thiadiazine-5-carboxylic acid (a) Benzyl 2-cyclohexyl-5,6-dihydro-4H-1,3,4-thiadiazine-5-carboxylate A solution of 2-bromoprop-2-enoic acid benzyl ester (1.68 g) in dry benzene (10.2 ml) was added to cyclohexane carbothioic acid hydrazide (1.0 g) in dry dimethylformamide (10 ml). The mixture was cooled to 0° and stirred, under an atmosphere of nitrogen, during the gradual addition of 1,5-diazabicyclo[4.3.0]non-5-ene (0.78 g) and then for a further 20 minutes at 0°. Ethyl acetate (100 ml) was added and the mixture was washed with brine and dried over magnesium sulphate The solvent was evaporated under reduced pressure and the resulting oil purified by flash chromatography using 10% ethyl acetate/90% petroleum ether as eluent to yield the sub-title product (1.0 g) as a pink solid.

A mass spectrum showed M+318 (base peak 91). $C_{17}H_{22}N_2O_2S$ Requires MWt 318.

(b) Benzyl 4-(3-acetylthio-1-oxopropyl)-2-cyclohexyl-5,6-dihydro-4H-1,3,4-thiadiazine-5-carboxylate 3-Acetylthiopropanoyl chloride (0.45 g) and poly-(4-vinylpyridine) (0.8 g) were added to a solution of the product of step a) (0.86 g) in dry toluene (20 ml). The mixture was stirred under an atmosphere of nitrogen for 20 hours. Diethyl ether (30 ml) was added and the mixture filtered. The filtrate was evaporated and the product purified by flash chromatography to yield the sub-title product (1.05 g) as a pale yellow oil.

Mass spectrum (FAB) showed M+449 (base peak 91). $C_{22}H_{28}N_2O_4S_2$ requires MWt 448.

(c) 2-Cyclohexyl-5,6-dihydro-4-(3-mercapto-1-oxopropyl)-4H-1,3,4-thiadiazine-5-carboxylic acid 1M Potassium hydroxide solution in methanol (5.83 ml) was added to a solution of the product of step (b) (0.87 g) in methanol (10 ml) and water (5 ml). The mixture was stirred under an atmosphere of nitrogen for 2 hours. Acetic acid was added and the solvent evaporated under reduced pressure. The mixture was purified by flash chromatography using 1% acetic acid/ethyl acetate as eluent to yield the title compound (0.24 g) as a white solid. mp 95°–97°.

Mass spectrum showed M+316 (base peak 156). $C_{13}H_{20}N_2O_3S_2$ requires MWt 316.

EXAMPLE 10

2,3-Dihydro-3-(3-mercapto-1-oxopropyl)-5-phenyl-1,3,4-oxadiazole-2-carboxylic acid (a) Ethyl benzoylhydrazono)acetate A solution of benzoyl hydrazine (1.4 g) and ethyl glyoxylate (1.32 g) in ethanol (50 ml) was stirred at room temperature for 24 hours. The solvent was evaporated and the residue treated with ether to give the sub-title product (1.8 g) as white solid. mp 140°–3°.

(b) 3-(Acetylthio)propionic anhydride

A solution of 3-(acetylthio)propionic acid (3.4 g) in ether (20 ml) was treated dropwise with a solution of dicyclohexylcarbodiimide (2.1 g) in ether with water-bath cooling. The mixture was stirred for 1.5 hours, filtered and the filtrate evaporated to give the sub-title product (3.2 g) as a yellow oil.

(c) Ethyl 3-(3-acetylthio-1-oxopropyl)-2,3-dihydro-5-phenyl-1,3,4-oxadiazole-2-carboxylate A mixture of the product from step a) (2.6 g) and the crude product from step b) (3.2 g) in pyridine (0.9 ml) was heated at 100° for 18 hours. The mixture was poured into water and extracted with ethyl acetate. The separated organic extract was washed with water, saturated aqueous sodium bicarbonate solution, water, dried and evaporated.

The residue was purified by flash chromatography to give the sub-title product (1.6 g) as a yellow oil.

A mass spectrum showed $M^{30}$ 350 (base peak 147) $C_{16}H_{18}N_2O_5S$ requires MWt 350.

(d) 2,3-Dihydro-3-(3-mercapto-1-oxopropyl)-5-phenyl-1,3,4-oxadiazole-2-carboxylic acid A solution of the product from step (c) (1.44 g) in methanol (40 ml) was cooled to 15° under nitrogen and treated dropwise with a solution of potassium hydroxide (0.69 g) in water (40 ml). The mixture was stirred at room temperature for 2 hours and then the solvents were evaporated. The residue was taken up in water and washed with ether. The aqueous phase was acidified with 2N HCl and extracted with ethyl acetate. The separated organic phase was washed with water, dried and evaporated. The residue was purified by flash chromatography to give a pale yellow solid. The solid was taken up in dichloromethane, treated with charcoal, filtered and the filtrate evaporated to give the title product (0.24 g) as an off-white solid. mp 106°–9°.

EXAMPLE 11

2,3-Dihydro-3-(3-mercapto-1-oxopropyl)-5-[4-(trifluoromethyl)phenyl]-1,3,4-thiadiazole-2-carboxylic acid (a) 4-(Trifluoromethyl)phenylcarbothioic acid hydrazide

[((4-(Trifluoromethyl)phenyl)thioxomethyl)thio]acetic acid (6.7 g) was dissolved in methanol (50 ml). Potassium hydroxide (1.34 g) in water (15 ml) was added followed by hydrazine hydrate (1.28 ml). The mixture was stirred for 4 hours at room temperature. Glacial acetic acid was added until the pH was 5 and the solvent was removed under reduced pressure. The product was extracted with diethyl ether (250 ml) and the solvent was evaporated under reduced pressure. The resulting solid was crystallised from cyclohexane as pale pink crystals (4.0 g) mp 114°–115.5°.

(b) Benzyl 2,3-dihydro-5-[4-(trifluoromethyl)phenyl]-1,3,4-thiadiazole-2-carboxylate Benzyl glyoxalate (0.8 g) was added to a solution of the product from step a) (1.0 g) in dry ethanol (30 ml). The mixture was stirred at room temperature under an atmosphere of nitrogen for 5 hours. The solvent was removed under reduced pressure and the product was crystallised from ethanol to yield the sub-title product (1.4 g) as white crystals. mp 99°–100.5°.

(c) Benzyl 3-[3-acetylthio-1-oxopropyl]-2,3-dihydro-5-[4(trifluoromethyl)phenyl]-1,3,4-thiadiazole-2-carboxylate 3-Acetylthiopropanoyl chloride (0.36 g), poly (4-vinyl pyridine) (0.8 g) and the product from step b) (0.8 g) were stirred together in dry toluene (30 ml) under an atmosphere of nitrogen for 20 hours. Diethyl ether was added and the solid was filtered off and washed with diethyl ether. The filtrate was evaporated under reduced pressure and the resulting product was crystallised from ethanol to yield the sub-title product (0.9 g) as a white solid. mp 120°–121°.

(d) 2,3-Dihydro-3-(3-mercapto-1-oxopropyl)-5-[4-(trifluoromethyl)phenyl]-1,3,4-thiadiazole-2-carboxylic acid Potassium hydroxide in methanol (1M, 4.9 ml) was added to a solution of the product from step c) (0.81 g) in methanol (10 ml) and water (5 ml). The mixture was stirred under an atmosphere of nitrogen for 2 hours. Glacial acetic acid was added and the solvent was removed under reduced pressure The product was purified by flash chromatography using 1% acetic acid/99% ethyl acetate as eluent to yield the title compound (0.23 g) as a fawn solid. mp softens 93°–75°.

A mass spectrum showed M+364 (base peak 231) $C_{13}H_{11}F_3Nhd\ 2O_3S_2$ requires MWt 364.

EXAMPLE 12

Benzyl 4-[3-acetylthio-1-oxopropyl]-5,6-dihydro-1-methyl-2-phenyl-4H-1,3,4-triazine-5-carboxylate (a) Benzyl 5,6-dihydro-1-methyl-2-phenyl-4H-1,3,4-triazine-5-carboxylate Benzenecarboximidic acid-N-methyl hydrazide monohydroiodide (0.43 g) in dry dimethylformamide (10 ml) and benzyl 2-bromo-prop-2-enoate (0.41 g) in benzene (2.5 ml) were cooled to 0° and stirred together under an atmosphere of nitrogen. A solution of 1,5-diazabicyclo[4.3.0]non-5-ene (0.4 ml) in dimethylformamide (5 ml) was added gradually and the mixture was stirred at 0° for a further 20 minutes. Ethyl acetate (100 ml) was added and the mixture was washed with brine (30 ml) and dried over magnesium sulphate. The solvent was removed at reduced pressure to yield the sub-title product (0.46 g) as an orange oil.

A mass spectrum showed M+309 (base peak 91).

A fast atom bombardment mass spectrum showed M+310 (base peak 91). $C_{18}H_{19}N_3O_2$ requires MWt 309.

(b) Benzyl 4-[3-acetylthio-1-oxopropyl]-5,6-dihydro-1-methyl-2-phenyl-4H-1,3,4-triazine-5-carboxylate 3-Acetylthiopropanoyl chloride (0.25 g), poly(4-vinyl pyridine) (0.4 g) and the product from step a) were stirred together in dry toluene (20 ml) under an atmosphere of nitrogen for 24 hours. Diethyl ether (20 ml) was added and the solid was filtered off and washed with diethyl ether. The filtrate was evaporated under reduced pressure. The resulting oil was purified by flash chromatography using 10% ethyl acetate/90% petroleum ether as eluent to yield the title compound (0.11 g) as an amber oil.

A mass spectrum showed M+439 (base peak 93). $C_{23}H_{25}N_3O_4S$ requires MWt 439.

NMR CDCl$_3$,delta: 1.84(S,3H), 2.31(S), 2.35–3.35(m), 4.41(m,lH), 5.15(m), 7.08–7.51 (m).

The following compounds were prepared from the appropriate starting materials by the processes described in Example 6.

EXAMPLE 13

5-t-Butyl-3-[N-(1-(S)-ethoxycarbonylbutyl)-L-alanyl]-2,3-dihydro-1,3,4-thiadiazole-2-(R)-carboxylic acid mp 67°–9°.

Found: C,48.37; H,7.99; N,9.42; S,7.2%. $C_{17}H_{29}N_3O_5S\cdot 2H_2O$ requires: C,48.22; H,7.80; N,9.93; S,7.57%.

EXAMPLE 14

5-t-Butyl-3-[N-(1-(R)-ethoxycarbonylbutyl)-L-alanyl]-2,3-dihydro 1,3,4-thiadiazole-2-(R)-carboxylic acid mp 67°–9°.

Found: C,51.44; H,7.52; N,10.38; S,7.79%. $C_{17}H_{29}N_3O_5S$. $0.5H_2O$ requires: C,51.52; H,7.58; N,10.61; S,8.08%.

EXAMPLE 15

5-t-Butyl-3-[N-(1-(R)-ethoxycarbonylbutyl)-L-alanyl]-2,3-dihydro-1,3,4-thiadiazole-2-(S)-carboxylic acid mp 124°–5°.

Found: C,52.46; H,7.63; N,10.77; S,8.07%. $C_{17}H_{29}N_3O_5S$. $0.5H_2O$ requires: C,52.71; H,7.49; N,10.85; S,8.27%.

The following compounds were prepared by the method of Example 5 (using appropriate starting materials).

EXAMPLE 16

3-[N-(1-(S)-Carboxy-3-phenylpropyl)-L-alanyl]-2,3-dihydro-5-phenyl-1,3,4-thiadiazole-2-(S)-carboxylic acid mp softens at 151°, decomposes at 165°–170°.

A fast atom bombardment mass spectrum showed $M^+442$ (base peak 91).

$C_{22}H_{23}N_3O_5S$ requires MWt 441.

EXAMPLE 17

5-t-Butyl-3-[N-(1-(S)-carboxy-3-phenylpropyl)-L-alanyl]-2,3-dihydro-1,3,4-thiadiazole-2-(S)-carboxylic acid mp softens at 161°, decomposes at 179°–184°.

A fast atom bombardment mass spectrum showed $M^+422$ (base peak 91). $C_{20}H_{27}N_3O_5S$ requires MWt 421

EXAMPLE 18

5-t-Butyl-3-[N-(1-(S)-carboxybutyl)-L-alanyl]-2,3-dihydro-1,3,4-thiadiazole-2-(S)-carboxylic acid mp 156°–9°.

The following compounds were prepared by the method of Example 4 (using appropriate starting materials).

EXAMPLE 19

5-Cyclohexyl-3-[N-1-(S)-ethoxycarbonyl-3-phenyl propyl)-L-alanyl]-2,3-dihydro-1,3,4-thiadiazole-2-(S)-carboxylic acid mp 136°–138°.

EXAMPLE 20

3-[N-(1-(S)-Ethoxycarbonyl-3-phenylpropyl)-L-alanyl]-2,3-dihydro-5-(pyridin-3-yl)-1,3,4-thiadiazole-2-(S)-carboxylic acid mp 160°–3° (softens at c. 140°).

EXAMPLE 21

3-[N-(1-(S)-Ethoxycarbonyl-3-phenylpropyl)-L-alanyl]-2,3-dihydro-5-isopropyl-1,3,4-thiadiazole-2-(S)-carboxylic acid

EXAMPLE 22

3-[N-(1-(S)-Ethoxycarbonyl-3-phenylpropyl]-L-alanyl]-2,3-dihydro-5-methyl-1,3,4-thiadiazole-2-(S)-carboxylic acid mp 161°–2°.

EXAMPLE 23

5-t-Butyl-3-[N2-(1-(S)-ethoxycarbonyl-3-phenyl propyl)-L-lysyl]-2,3-dihydro-1,3,4-thiadiazole-2-(S)-carboxylic acid hydrochloride A solution of 5-t-butyl-3-[$N^2$-(1-(S)-ethoxycarbonyl-3-phenylpropyl)-L-lysyl]-2,3-dihydro-1,3,4-thiadiazole-2-(S)-carboxylic acid (0.97 g, prepared using the appropriate starting material by the process of Example 4) in tetrahydrofuran (20 ml) and water (20 ml) was treated with 1N hydrochloric acid (3.8 ml). The solvents were evaporated and the residue was taken up in a mixture of dichloromethane and toluene. The solvents were removed by evaporation to give the title product (0.9 g) as a white A mass spectrum (FAB) showed $M^+507$ (base peak 84). $C_{25}H_{38}N_4O_5S$ requires MWt 506.

EXAMPLE 24

5-t-Butyl-3-[N-(1-(S)-ethoxycarbonyl-3-phenylpropyl)-L-alanyl]-2,3-dihydro-1,3,4-thiadiazole-2-(R)-carboxylic acid Prepared from the product of Example 4 step b) by the process of Example 4 step d).

mp 60°–63°.

EXAMPLE 25

3-[N-(1-(S)-Ethoxycarbonyl-3-phenylpropyl)-L-alanyl]-2,3-dihydro-5-(morpholin-4-yl)-1,3,4-thiadiazole-2-(S)-carboxylic acid maleic acid salt A solution of 3-[N-(1-(S)-ethoxycarbonyl-3-phenylpropyl)-L-alanyl]-2,3-dihydro-5-(morpholin-4-yl)-1,3,4-thiadiazole-2-(S)-carboxylic acid (0.47 g) (prepared from the appropriate starting materials by the process of Example 4) in ethanol (25 ml) was treated with maleic acid (0.11 g). The solvent was removed by evaporation. Trituration of the residue with acetonitrile gave the title product as a white solid (0.31 g). mp 174°–175°.

The following compounds were prepared by the method of Example 3 using appropriate starting materials.

EXAMPLE 26

5-t-Butyl-2,3-dihydro-3-(3-mercapto-1-oxopropyl)-1,3,4-thiadiazole-2-carboxylic acid mp 128°.

EXAMPLE 27

2,3-Dihydro-3-(3-mercapto-1-oxopropyl)-5-(4-methoxyphenyl)-1,3,4-thiadiazole-2-carboxylic acid mp 164°

EXAMPLE 28

Ethyl 3-(3-acetylthio-1-oxopropyl)-2,3-dihydro-5-methylamino-1,3,4-thiadiazole-2-carboxylate mp 102°–103°.

A mass spectrum showed M+319 (base peak 116). $C_{11}H_{17}N_3O_4S_2$ requires MWt 319.

EXAMPLE 29

2,3-Dihydro-3-(3-mercapto-1-oxypropyl)-5-(2-methyl phenyl)-1,3,4-thiadiazole-2-carboxylic acid mp 118°–120°.

EXAMPLE 30

5-(Furan-2-yl)-2,3-dihydro-3-(3-mercapto-1-oxopropyl)1,3,4-thiadiazole-2-carboxylic acid mp 105°–108°.

EXAMPLE 31

Ethyl 3-(3-acetylthio-1-oxopropyl)-5-(4-chlorophenyl)-2,3-dihydro-1,3,4-thiadiazole-2-carboxylate Prepared by similar processes to those of Example 3 steps (a) and (b). The product was isolated as a clear gum.

NMR spectrum (CDCl₃) of the compound showed characteristic peaks at delta 7.50 (4H,q,aromatic C$\underline{H}$s), delta 2.34 (3H,s,-SCOC$\underline{H}_3$) and delta 6.30 (1H,s, heterocyclic C$\underline{H}$).

EXAMPLE 32

Benzyl 3-(3-acetylthio-1-oxopropyl)-5-benzyl-2,3-dihydro-1,3,4-thiadiazole-2-carboxylate Prepared using appropriate starting materials by process of Example 3 steps a) and b). The product was isolated as an oil.

NMR spectrum (CDCl₃) showed a characteristic signal at delta 6.17 (1H,s,heterocyclic C$\underline{H}$).

EXAMPLE 33

Benzyl 3-(3-acetylthio-1-oxopropyl)-2,3-dihydro-5-(2-phenylethyl)-1,3,4-thiadiazole-2-carboxylate Prepared by similar processes to those of Example 3 steps (a) and (b). The product was isolated as an oil.

NMR spectrum (CDCl₃) showed a characteristic signal at delta 6.10 (1H,s,heterocyclic CH).

EXAMPLE 34

Ethyl 3-(3-acetylthio-1-oxopropyl)-2,3-dihydro-5-(naphthalen- 2-yl)-1,3,4-thiadiazole-2-carboxylate (a) Naphthalene-2-carbothioic acid hydrazide The sub-title product was prepared from appropriate starting materials by the processes of Example 7, steps (a), (b), (c) and (d). mp 166°–167°.

(b) Ethyl 2,3-dihydro-5-(naphthalen-2-yl)-1,3,4-thiadiazole-2-carboxylate

Prepared from the product of step a) and ethyl glyoxylate by the process of Example 3, step a). The crude product was used without further purification.

(c) Ethyl 3-(3-acetylthio-1-oxopropyl)-2,3-dihydro-5-(naphthalen-2-yl)-1,3,4-thiadiazole-2-carboxylate Prepared from the crude product of step (b) and 3-acetylthiopropanoyl chloride by the process of Example 3, step (b). mp 107°–108°

Mass spectrum (FAB) showed M+417 (base peak 213). $C_{20}H_{20}N_2O_4S_2$ requires MWt 416.

EXAMPLE 35

5-(Adamant-1-yl)-2,3-dihydro-3-(3-mercapto-1-oxopropyl)-1,3,4-thiadiazole-2-carboxylic acid (a) Methyl 1-adamantanecarbodithioate A mixture of 1-adamantanecarboxylic acid chloride (9.0 g) and 2,4-bis-methylthio-1,2,3,4-dithiaphosphetan-2,4-disulphide (12.9 g) in dry benzene was heated under reflux for 5 hours. The solvent was evaporated and the residue purified by flash chromatography to give the sub-title product (6.2 g) as a yellow solid.

mp 64.5°–66°.

(b) Adamantane-1-carbothioic acid hydrazide

A solution of the product of step (a) (1 g) in methanol (50 ml) was treated with hydrazine hydrate (0.3 g) and the mixture stirred at room temperature for 1 hour. The solvent was evaporated, the residue triturated with water, and the pH adjusted to 7 to give the sub-title product (0.8 g) as a white solid.

mp 204°–206°.

(c) Ethyl 5-(adamant-1-yl)-2,3-dihydro-1,3,4-thiadiazole-2-carboxylate

The product of step (b) was treated with ethyl glyoxylate by the process of Example 3, step (a) to give the sub-title product (1.5 g) as an oil.

(d) Ethyl 5-(adamant-1-yl)-2,3-dihydro-3-(3-mercapto-1-oxopropyl)-1,3,4-thiadiazole-2-carboxylate The crude product of step (c) was treated with 3-acetylthiopropanoyl chloride by the process of Example 3, step (b) to give the sub-title product as an oil.

Mass spectrum (FAB) showed M+425 (base peak 221). $C_{20}H_{28}N_2O_4S_2$ required MWt 424.

(e) 5-(Adamant-1-yl)-2,3-dihydro-3-(3-mercapto-1-oxopropyl)-1,3,4-thiadiazole-2-carboxylic acid The product of step (d) was treated with potassium hydroxide by the process of Example 3, step (c) to give the title product as white solid. mp 183°–184°. Mass spectrum (FAB) showed M+355 (base peak 221). $C_{16}H_{22}N_2O_3S_2$ requires MWt 354.

EXAMPLE 36

2,3-Dihydro-3-(3-mercapto-1-oxopropyl)-5-methyl-1,3,4-thiadiazole-2-carboxylic acid dicyclohexylamine salt A solution of dicyclohexylamine (0.5 ml) in ether (10 ml) was added to a solution of 2,3-dihydro-3-(3-mercapto-1-oxopropyl)-5-methyl-1,3,4-thiadiazole-2- -carboxylic acid (0.5 g) (prepared from appropriate starting materials by the method of Example 3) in ether (20 ml). The solvent was removed by evaporation.

Trituration of the residue with ether gave the title compound as a white solid (0.5 g). mp 150°–153°

The following compounds were prepared by the method of Example 36 using appropriate starting materials

EXAMPLE 37

5-Cyclohexyl-2,3-dihydro-3-(3-mercapto-1-oxopropyl)-1,3,4-thiadiazole-2-carboxylic acid dicyclohexylamine salt mp 174°–6°.

EXAMPLE 38

2,3-Dihydro-3-(3-mercapto-1-oxopropyl)-5-methylthio-1,3,4-thiadiazole-2-carboxylic acid dicyclohexylamine salt mp 150°–3°.

EXAMPLE 39

Benzyl 3-[N-(1-(S)-ethoxycarbonyl-3-phenylpropyl)-L-alanyl]-2,3-dihydro-5-methylthio-1,3,4-thiadiazole-2-(S)-carboxylate Prepared by similar processes to those of Example 1 from appropriate starting materials. The product was isolated as a clear gum.

The nmr spectrum of the compound showed characteristic signals at delta 2.55 (3H,s,-SCH$_3$) and 6.32 (1H,s,heterocyclic CH).

EXAMPLE A

In vitro Assay of inhibitors of Angiotensin Converting Enzyme

The method is based upon that of Cushman and Cheung (1971) but uses a radioactive substrate [glycine-1-$^{14}$C]hippuryl-L-histidyl-L-leucine (HHL) whose hydrolysis may be determined by liquid scintillation counting of released [$^{14}$C]-hippuric acid. Hydrolysis of 2 mM HHL by an extract of rabbit lung acetone powder (Sigma) over a 30 min. incubation period at 37° is followed by acidification of the reaction mixture and extraction of [$^{14}$C]hippurate with ethyl acetate.

Potential inhibitors are tested initially at 0.01 mM and if found active are retested at lower concentrations to determine an IC$_{50}$. Dimethyl sulphoxide at 1% final concentration may be used as a solubility aid without affecting enzyme activity. Compounds of special interest are studied at a range of substrate and inhibitor concentrations to determine the type of inhibition and are also tested against other enzymes, e.g. carboxypeptidase A to establish their specificity for ACE.

EXAMPLE B

Antihypertensive effects were investigated in conscious spontaneously hypertensive rats (SHR) of the Okamoto strain. Systolic blood pressure and heart rate were measured by the tail cuff method using an electrosphygmomanometer 1 hour before and 1, 3, 5 and 24 hours after oral dosing with the compound (dose range 0.1–100 mg/kg p.o.). Percentage changes in each parameter were measured with respect to pretreatment control values.

| Example C | | |
|---|---|---|
| | % w/w | Range % w/w |
| Compound of formula I | 5 | 1–20 |
| Microcrystalline cellulose | 50 | 10–80 |
| Spray dried lactose | 37.75 | 10–80 |
| Magnesium stearate | 1 | 0.25–2 |
| Colloidal silicon dioxide | 0.25 | 0.1–1 |
| Cross linked sodium carboxy methyl cellulose | 3 | 1–5 |
| Hydroxypropyl methyl cellulose (coating) | 3 | 1–5 |

This formulation is made up as a direct compression tablet, or without compression or coating, may be filled into a gelatine capsule.

| Example D | | |
|---|---|---|
| | % w/w | Range % w/w |
| Compound of formula I | 5 | 1–20 |
| Microcrystalline cellulose | 50 | 10–80 |
| Lactose | 35.75 | 10–80 |
| Polyvinylpyrrolidone | 2 | 1–5 |
| Magnesium stearate | 1 | 0.25–2 |
| Colloidal silicon dioxide | 0.25 | 0.1–1 |
| Cross linked sodium carboxy methyl cellulose | 3 | 1–5 |
| Hydroxypropyl methyl cellulose (coating) | 3 | 1–5 |

This formulation is made up as a granulate and then compressed into a tablet. Alternatively the granules may be filled into a gelatine capsule.

We claim:

1. A compound of formula I

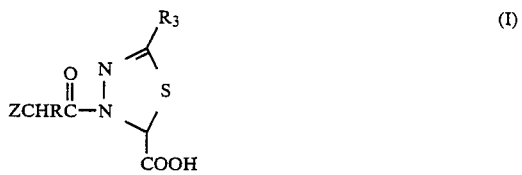

in which R$_3$ is hydrogen, alkyl, C$_{1-10}$, cycloalkyl C$_{3-10}$, CF$_3$, SR$_{10}$, or a heterocyclic group selected from pyridyl, furyl and morpholinyl, said heterocyclic group being optionally substituted by alkyl C$_{1-6}$, halogen, alkoxy C$_{1-6}$, nitro, nitrile, CF$_3$, SR$_6$, NR$_7$R$_{11}$ or hydroxy, R$_3$ may also be adamantyl, methylamino, benzyl, naphthyl and phenyl optionally substituted by methylthio, methoxy, methyl, ethyl, chloro or CF$_3$.

R$_6$, R$_7$ and R$_{11}$, which may be the same or different, are each hydrogen or alkyl C$_{1-10}$, R$_{10}$ is alkyl C$_{1-10}$, R is hydrogen, alkyl C$_{1-10}$ or alkyl C$_{1-6}$ substituted by NH$_2$, Z is R$_2$CH(COOH)NH- or R$_1$SCH$_2$R$_1$ is hydrogen or R$_8$CO-, R$_8$ is alkyl C$_{1-10}$ or phenyl, and R$_2$ is alkyl C$_{1-10}$ or phenylalkyl C$_{7-12}$ and pharmaceutically acceptable salts, esters and amides thereof.

2. A compound according to claim 1, wherein Z is R$_2$CH(COOH)NH-.

3. A compound according to claim 2, wherein the —COOH group of the Z-substituent is present as a C 1 to 6 alkyl ester.

4. A compound according to claim 3, wherein the ester is an ethyl ester.

5. A compound according to claim 2, wherein the carbon atom to which the —COOH group of the Z-substituent is attached is in the S configuration.

6. A compound according to claim 1, wherein R is alkyl C 1 to 6 or aminoalkyl C 1 to 6.

7. A compound according to claim 6, wherein R is aminobutyl.

8. A compound according to claim 1, wherein the carbon atom to which R is attached is in the S configuration.

9. A compound according to claim 1, wherein R$_2$ is alkyl C 1 to 6 or phenylalkyl C7 to 9.

10. A compound according to claim 9, wherein R$_2$ is n-propyl or phenylethyl.

11. A compound according to claim 1, wherein $R_8$ is alkyl C 1 to 10.

12. A compound according to claim 1, wherein $R_3$ is selected from methyl, pyridyl, furyl, methoxy, methylthio, t-butyl, isopropyl, cyclohexyl, morpholinyl, adamantyl, methylamino, benzyl, naphthyl and phenyl optionally substituted by methylthio, methoxy, methyl, ethyl, chloro or $CF_3$.

13. A compound according to claim 1, wherein $R_3$ is alkyl C 1 to 10 or cycloalkyl C3 to 10.

14. A compound according to claim 1, wherein
Z is $R_2CH(COOH)NH-$,
R is methyl or aminobutyl,
$R_2$ is n-propyl or phenylethyl,
$R_3$ is t-butyl, and
all asymmetric carbon atoms are in the S configuration.

15. A compound according to claim 1, selected from,
5-t-Butyl-3-[N-(1-(S)-ethoxycarbonyl-3-phenylpropyl)-L-alanyl]-2,3-dihydro-1,3,4-thiadiazole-2-(S)-carboxylic acid,
5-t-Butyl-3-[N²-(1-(S)-carboxy-3-phenylpropyl)-L-alysyl]-2,3-dihydro-1,3,4-thiadiazole-2-(S)-carboxylic acid, and
5-t-Butyl-3-[N-(1-(S)-ethoxycarbonylbutyl)-L-alanyl]-2,3-dihydro-1,3,4-thiadiazole-2-(S)-carboxylic acid,
and pharmaceutically acceptable salts, thereof.

16. A compound selected from the group consisting of:
3-[N-(1-(S)-Ethoxycarbonyl-3-phenylpropyl)-L-alanyl]-2,3-dihydro-5-phenyl-1,3,4-thiadiazole-2-(S)-carboxylic acid,
Benzyl 3-[N-(1-(S)-ethoxycarbonyl-3-phenylpropyl)-L-alanyl]-2,3-dihydro-5-phenyl-1,3,4-thiadiazole-2-(R)-carboxylate,
Benzyl 3-[N-(1-(S)-ethoxycarbonyl-3-phenylpropyl)-L-alanyl-]-2,3-dihydro-5-phenyl-1,3,4-thiadiazole-2-(S)-carboxylate,
3-[N-(1-(S)-Ethoxycarbonyl-3-phenylpropyl)-L-alanyl]-2,3-dihydro-5-phenyl-1,3,4-thiadiazole-2-(R)-carboxylic acid,
2,3-Dihydro-3-(3-mercapto-1-oxopropyl)-5-phenyl-1,3,4-thiadiazole-2-carboxylic acid,
Ethyl 3-(3-acetylthio-1-oxopropyl)-2,3-dihydro-5-phenyl-1,3,4-thiadiazole-2-carboxylate, acid,
Benzyl 5-t-Butyl-3-[N-(1-(S)-ethoxycarbonyl-3-phenylpropyl)-L-alanyl]-2,3-dihydro-1,3,4-thiadiazole-2-(S)-carboxylic acid,
Benzyl 5-t-butyl-3-[N-(1-(S)-ethoxycarbonyl-3-phenylpropyl)-L-alanyl]-2,3-dihydro-1,3,4-thiadiazole-2-(R)-carboxylate,
Benzyl 5-t-butyl-3-[N-(1-(S)-ethoxycarbonyl-3-phenyl propyl)-L-alanyl]-2,3-dihydro-1,3,4-thiadiazole-2-(S)-carboxylate,
5-t-Butyl-3-[N²-(1-(S)-carboxy-3-phenylpropyl)-L-lysyl]-2,3-dihydro-1,3,4-thiadiazole-2-(S)-carboxylic acid,
Benzyl 3-[N⁶-benzyloxycarbonyl-N²-(1-(S)-benzyloxycarbonyl-3-phenylpropyl)-L-lysyl]-5-t-butyl-2,3-dihydro-1,3,4-thiadiazole-2-(R)-carboxylate,
Benzyl 3-[N⁶-benzyloxycarbonyl-N2-(1-(S)-benzyloxycarbonyl-3-phenylpropyl)-L-lysyl]-5-t-butyl-2,3- dihydro-1,3,4-thiadiazole-2-(S)-carboxylate,
5-t-Butyl-3-[N-(1-(S)-ethoxycarbonylbutyl)-L-alanyl]- 2,3-dihydro-1,3,4-thiadiazole-2-(S)-carboxylic acid,
Benzyl 5-t-butyl-3-[N-(1-(S)-ethoxycarbonylbutyl)-L-alanyl]-2,3-dihydro-1,3,4-thiadiazole-2-(R)-carboxylate,
Benzyl 5-t-butyl-3-[N-(1-(S)-ethoxycarbonylbutyl)-L-alanyl]-2,3-dihydro-1,3,4-thiadiazole-2-(S)-carboxylate,
3-[N-(1-(S)-Ethoxycarbonyl-3-phenylpropyl)-L-alanyl]-2,3-dihydro-5-[4-(methylthio)phenyl]-1,3,4-thiadiazole-2-(S)-carboxylic acid,
t-Butyl 3-[N-(1-(S)-ethoxycarbonyl-3-phenylpropyl)-L-alanyl]-2,3-dihydro-5-[4-(methylthio)phenyl]-1,3,4-thiadiazole-2-(S)-carboxylate,
2,3-Dihydro-3-(3-mercapto-2-(S)-methyl-1-oxopropyl)-5-phenyl-1,3,4-thiadiazole-2-(S)-carboxylic acid,
Benzyl 3-(3-acetylthio-2-(S)-methyl-1-oxopropyl)-2,3-dihydro-5-phenyl-1,3,4-thiadiazole-2-carboxylate,
2,3-Dihydro-3-(3-mercapto-1-oxopropyl)-5-[4-(trifluoromethyl)phenyl]-1,3,4-thiadiazole-2-carboxylic acid,
Benzyl 3-[3-acetylthio-1-oxopropyl]-2,3-dihydro-5-[4trifluoromethyl)phenyl]-1,3,4-thiadiazole-2-carboxylate,
5-t-Butyl-3-[N-(1-(S)-ethoxycarbonylbutyl)-L-alanyl]-2,3-dihydro-1,3,4-thiadiazole-2-(R)-carboxylic acid,
5-t-Butyl-3-[N-(1-(R)-ethoxycarbonylbutyl)-L-alanyl]-2,3-dihydro-1,3,4-thiadiazole-2-(R)-carboxylic acid,
5-t-Butyl-3-[N-(1-(R)-ethoxycarbonylbutyl)-L-alanyl]-2,3-dihydro-1,3,4-thiadiazole-2-(S)-carboxylic acid,
3-[N-(1-(S)-Carboxy-3-phenylpropyl)-L-alanyl]-2,3-dihydro-5-phenyl-1,3,4-thiadiazole-2-(S)-carboxylic acid,
5-t-Butyl-3-[N-(1-(S)-carboxy-3-phenylpropyl)-L-alanyl]-2,3-dihydro-1,3,4-thiadiazole-2-(S)-carboxylic acid,
5-t-Butyl-3-[N-(1-(S)-carboxybutyl)-L-alanyl]-2,3-dihydro-1,3,4-thiadiazole-2-(S)-carboxylic acid,
5-Cyclohexyl-3-[N-(1-(S)-ethoxycarbonyl-3-phenyl propyl)-L-alanyl]-2,3-dihydro-1,3,4-thiadiazole-2-(S)-carboxylic acid,
3-[N-(1-(S)-Ethoxycarbonyl-3-phenylpropyl)-L-alanyl]-2,3-dihydro-5-(pyridin-3-yl)-1,3,4-thiadiazole-2-(S)-carboxylic acid,
3-[N-(1-(S)-Ethoxycarbonyl-3-phenylpropyl)-L-alanyl]-2,3-dihydro-5-isopropyl-1,3,4-thiadiazole-2-(S)-carboxylic acid,
5-t-Butyl-3-[N2-(1-(S)-ethoxycarbonyl-3-phenyl propyl)-L-lysyl]-2,3-dihydro-1,3,4-thiadiazole-2-(S)-carboxylic acid,
5-t-Butyl-3-[N-(1-(S)-ethoxycarbonyl-3-phenylpropyl)-L-alanyl]-2,3-dihydro-1,3,4-thiadiazole-2-(R)-carboxylic acid,
3-[N-(1-(S)-Ethoxycarbonyl-3-phenylpropyl)-L-alanyl]-2,3-dihydro-5-methyl-1,3,4-thiadiazole-2-(S)-carboxylic acid,
3-[N-(1-(S)-Ethoxycarbonyl-3-phenylpropyl)-L-alanyl]-2,3-dihydro-5-(morpholin-4-yl)-1,3,4-thiadiazole-2-(S)-carboxylic acid,
5-t-Butyl-2,3-dihydro-3-(3-mercapto-1-oxopropyl)-1,3,4-thiadiazole-2-carboxylic acid, 2,3-Dihydro-3-(3-mercapto-1-oxopropyl)-5-(4-methoxyphenyl)-1,3,4-thiadiazole-2-carboxylic acid, Ethyl 3-(3-acetylthio-1-oxopropyl)-2,3-dihydro-5-methylamino-1,3,4-thiadiazole-2-carboxylate, 2,3-Dihydro-3-(3-mercapto-1-oxypropyl)-5-(2-methylphenyl)-1,3,4-thiadiazole-2-carboxylic acid, 5-(Furan-2-yl)-2,3-dihydro-3-(3-mercapto-1-oxopropyl)-1,3,4-thiadiazole-2-carboxylic acid, Ethyl 3-(3-acetylthio-1-oxopropyl)-5-(4-chlorophenyl)-2,3-dihydro-1,3,4-thiadiazole-2-carboxylate, Benzyl 3-(3-acetylthio-1-oxopropyl)-5-benzyl-2,3-dihydro-1,3,4-thiadiazole-2-carboxylate, Benzyl 3-(3-acetylthio-1-oxopropyl)-2,3-dihydro-5-(2-phenylethyl)-1,3,4-thiadiazole-2-carboxylate, Ethyl 3-(3-acetylthio-1-oxopropyl)-2,3-dihydro-5-(naphthalen-2-yl)-1,3,4-thiadiazole-2-carboxylate, 5-(Adamant-1-yl)-2,3-dihydro-3-(3-mercapto-1-oxopropyl)-1,3,4-thiadiazole-2-carboxylic acid, Ethyl 5-(adamant-1-yl)-2,3-dihydro-3-(3-mercapto-1-oxopropyl)-1,3,4-thiadiazole-2-carboxylate, 2,3-Dihydro-3-(3-mercapto-1-oxopropyl)-5-methyl-1,3,4-thiadiazole-2-carboxylic acid, 5-Cyclohexyl-2,3-dihydro-3-(3-mercapto-1-oxopropyl)-1,3,4-thiadiazole-2-carboxylic acid, 2,3-Dihydro-3-(3-mercapto-1-oxopropyl)-5-methylthio-1,3,4-thiadiazole-2-carboxylic acid, and Benzyl 3-[N-(1-(S)-ethoxycarbonyl-3-phenylpropyl)-L-alanyl]-2,3-dihydro-5-methylthio-1,3,4-thiadiazole-2-(S)-carboxylate, carboxylate, and pharmaceutically acceptable salts thereof.

17. A method of treatment of a hypertensive condition which comprises administration of an effective amount of a compound according to claim 1 to a patient suffering from such a condition.

18. A pharmaceutical formulation for treating a hypertensive condition comprising a therapeutically effective amount of a compound according to claim 1 in admixture with a pharmaceutically acceptable adjuvant, diluent or carrier.

19. A compound of formula II,

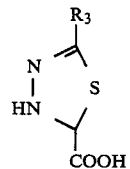

II in which $R_3$ is hydrogen, alkyl $C_{1-10}$, cycloalkyl $C_{3-10}$, $CF_3$, $SR_{10}$, or a heterocyclic group selected from pyridyl, furyl, and morpholinyl, said heterocyclic group being optionally substituted by alkyl $C_{1-6}$, halogen, alkoxy $C_{1-6}$, nitro, nitrile, $CF_3$, $SR_6$, $NR_7R_{11}$ or hydroxy, $R_6$, $R_7$, and $R_{11}$, which may be the same or different, are each hydrogen or alkyl $C_{1-10}$, $R_{10}$ is alkyl $C_{1-10}$, and pharmaceutically acceptable salts, esters, amides and tautomers thereof.

* * * * *